US009157914B2

(12) United States Patent
Sreenivasan

(10) Patent No.: US 9,157,914 B2
(45) Date of Patent: Oct. 13, 2015

(54) METHODS OF MODULATING CELL SURFACE RECEPTORS TO PREVENT OR REDUCE INFLAMMATION

(75) Inventor: Prem Sreenivasan, Westfield, NJ (US)

(73) Assignee: Colgate-Palmolive Company, New York, NY (US)

( * ) Notice: Subject to any disclaimer, the term of this patent is extended or adjusted under 35 U.S.C. 154(b) by 1327 days.

(21) Appl. No.: 11/620,880

(22) Filed: Jan. 8, 2007

(65) Prior Publication Data

US 2007/0160544 A1    Jul. 12, 2007

Related U.S. Application Data

(60) Provisional application No. 60/757,751, filed on Jan. 10, 2006.

(51) Int. Cl.
| | | |
|---|---|---|
| *C12Q 1/04* | (2006.01) | |
| *G01N 33/569* | (2006.01) | |
| *G01N 33/68* | (2006.01) | |
| *G01N 21/64* | (2006.01) | |

(52) U.S. Cl.
CPC ............ *G01N 33/56955* (2013.01); *C12Q 1/04* (2013.01); *G01N 33/6863* (2013.01); *G01N 2021/6439* (2013.01); *G01N 2500/00* (2013.01); *G01N 2500/10* (2013.01); *G01N 2800/18* (2013.01); *G01N 2800/26* (2013.01)

(58) Field of Classification Search
USPC ............................................... 424/49; 435/34
See application file for complete search history.

(56) References Cited

U.S. PATENT DOCUMENTS

| | | |
|---|---|---|
| 3,538,230 A | 11/1970 | Pader et al. |
| 4,358,437 A | 11/1982 | Duke |
| 5,288,480 A | 2/1994 | Gaffar et al. |
| 5,578,295 A | 11/1996 | Francis |
| 5,703,123 A | 12/1997 | Pelzer et al. |
| 7,005,225 B2 | 2/2006 | Qian et al. |
| 7,005,255 B2 | 2/2006 | Kaddurah-Daouk et al. |
| 7,329,489 B2 | 2/2008 | Kaddurah-Daouk et al. |
| 7,550,258 B2 | 6/2009 | Kaddurah-Daouk et al. |
| 7,635,556 B2 | 12/2009 | Kaddurah-Daouk et al. |
| 2002/0086282 A1 | 7/2002 | Pillarisetti et al. |
| 2003/0078246 A1 | 4/2003 | Sackeyfio et al. |
| 2004/0048797 A1 | 3/2004 | Miller et al. |
| 2004/0224876 A1 | 11/2004 | Jost-Price |
| 2005/0014132 A1 | 1/2005 | Kaddurah-Daouk et al. |
| 2005/0113345 A1 | 5/2005 | Chow et al. |
| 2006/0134676 A1 | 6/2006 | Kaddurah-Daouk et al. |
| 2006/0134677 A1 | 6/2006 | Kaddurah-Daouk et al. |
| 2006/0134678 A1 | 6/2006 | Kaddurah-Daouk et al. |
| 2006/0141421 A1 | 6/2006 | Braunecker et al. |
| 2007/0072203 A1 | 3/2007 | Kaddurah-Daouk et al. |
| 2007/0160544 A1* | 7/2007 | Sreenivasan ................... 424/49 |
| 2008/0027146 A1 | 1/2008 | Fiorellini et al. |

FOREIGN PATENT DOCUMENTS

| | | |
|---|---|---|
| EP | 0528468 A1 | 2/1993 |
| EP | 1057809 | 12/2000 |
| EP | 1210928 | 6/2002 |
| EP | 0863402 | 9/2005 |
| EP | 1738643 | 1/2007 |
| EP | 1925292 | 5/2008 |
| GB | 2401865 | 11/2004 |
| WO | 9513094 A | 5/1995 |
| WO | WO 97/16542 | 5/1997 |
| WO | WO 97/47282 | 12/1997 |
| WO | WO 00/24776 | 5/2000 |
| WO | 0148481 A1 | 7/2001 |
| WO | 0155386 A | 8/2001 |
| WO | WO 01/85116 | 11/2001 |
| WO | WO 03/022993 | 3/2003 |
| WO | WO2005/039504 | 5/2005 |
| WO | 2005057222 A | 6/2005 |
| WO | WO 2005/103071 | 11/2005 |
| WO | WO 2008/093072 | 7/2008 |
| WO | WO 2009/048841 | 4/2009 |

OTHER PUBLICATIONS

Nixon et al. Infection and Immunity vol. 68, No. 9, p. 5284-5292 ( Sep. 2000).*
Lapp et al. ,J. Periodontology 76, 803-812 (May 2005).*
Rangsini et al. , Journal of Periodontal Research vol. 37, No. 3, pp. 177-183 (Jun. 2002).*
Page, R., J. Periodont. Res. 1991, 26, 230-242 . . . .*
Rossomando et al., J. Periodont. 1993, 64, 445-449.*
Tatakis et al. "Etiology and Pathogenesis of Periodontal Diseases". *The Dental Clinics of North America*. vol. 49. (2005) pp. 491-516.
Holt, R et al., "Dental damage, sequelae, and prevention," The Western Journal of Medicine (2001) 174:4 pp. 288-290 ISSN: 0093-0415 XP002443683 abstract.
Uehara, A et al., "Priming of human oral epithelial cells by interferon-gamma to secrete cytokines in response to lipopolysaccharides, lipoteichoic acids and peptidoglycans," Journal of Medical Microbiology (2002) 51:8 pp. 626-634, ISSN: 0022-2615 XP002434615 abstract.
Weinberg, A et al., "Epithelial Antimicrobial Peptides: Review and Significance for Oral applications," Critical Reviews in Oral Biology and Medicine, CRC Press, Boca Raion, FL, US (1998) 9:4 pp. 399-414, XP000972953 ISSN: 1045-4411 Abstract.

(Continued)

*Primary Examiner* — David J Steadman

(57) ABSTRACT

The invention includes a method of distinguishing among oral bacteria species to determine whether a species is orally deleterious. Such method includes contacting at least one bacterium or portion of a bacterium of a species of oral bacteria a gingival cell; and detecting the presence of an indicator compound. The substantial absence of an indicator material signifies that the species of bacteria is not a deleterious species. Also included within the scope of the invention are methods for determining the anti-inflammatory effect of an agent. Such methods include contacting the cell with the agent in the presence of a deleterious bacterium or portion of such bacterium and detecting the presence of an indicator compound. The substantial absence of an indicator material signifies that agent is an anti-inflammatory agent.

7 Claims, 2 Drawing Sheets

(56) References Cited

OTHER PUBLICATIONS

Madianos, P. N. et al., "Generation of inflammatory stimuli: how bacteria set up inflammatory responses in the gingiva," Journal of Clinical Periodontology, (2005) 32:6 pp. 57-71 XP002435073, ISSN: 0303-6979 abstract.

Uehara, A et al., "Contrasting Responses of Human Gingival and Colonic Epithelial Cells to Lipopolysaccharides, Lipoteichoic Acids and Peptidoglycan in the Presence of Soluble CD14," Medical Microbiology and Immunology, Berlin, DE (2001) 189:4 pp. 185-192, XP009078055 abstract.

Sugawara Shunji, et al., "Innate Immune Responses in Oral Mucosa," Journal of Endotoxin Research, Churchill Livingston,of Edinburgh, GB (2002) 8:6 pp. 465-468, XP009078070, ISSN: 0968-0519 Abstract.

Ogawa Tomohiko, et al., "Cell activation by Porphyromonas gingivalis lipid A molecule through Toll-like receptor 4- and myeloid differentiation factor 88-dependent signaling pathway," International Immunology, (2002) 14:11 pp. 1325-1332, XP002434613 ISSN: 0953-8178 Abstract.

Wang P-L, et al., "Porphyromonas gingivalis lipopolysaccharide signaling in gingival fibroblasts-CD14 and Toll-like receptors," Critical Reviews in Oral Biology and Medicine: An Official Publication of the American Association of Oral Biologists, (2002) 13:2 pp. 132-142 XP002434614, ISSN: 1045-4411 Abstract.

International Search Report Dated Aug. 2, 2007.

Putnins, Edward E. et al., "Induction of Keratinocyte Growth Factor 1 Expression by Lipopolysaccharide is Regulated by CD-14 and Toll-Like Receptors 2 and 4," Infection and Immunity (2002) pp. 6541-6548 70:12.

Search Report from the European Patent Office for corresponding European Patent Application No. EP 10 15 3338 dated Aug. 3, 2010.

Afflitto et al., 1989, "Salivary and plaque triclosan levels after brushing with a 0.3% triclosan/copolymer/NaF dentifrice," Amer. J. Dent. 2:207-210.

Akalin et al., 2007, "Lipid Peroxidation Levels and Total Oxidant Status in Serum, Saliva and Gingival Crevicular Fluid in Patients with Chronic Periodontitis," J. Clin. Periodontol. 34(7):558-265.

Armitage, 2004, "Analysis of Gingival Crevice Fluid and Risk of Progression of Periodontitis," Periodontol. 34:109-119.

Back et al., 2007, "Increased Leukotriene Concentrations in Gingival Crevicular Fluid from Subjects with Periodontal Disease and Atherosclerosis," Atherosclerosis 193(2):389-394.

Bergamini et al., 2004, "Oxygen, Reactive Oxygen Species and Tissue Damage," Curr. Pharm. Des. 10(14):1611-1626.

Berry et al., 2004, "Xanthine Oxidoreductase and Cardiovascular Disease: Molecular Mechanisms and Pathophysiological Implications," J. Physiol. 555(Pt. 3):589-606.

Bodet et al., 2005, "Modulation of cytokine production by Porphyromonas gingivalis in a macrophage and epithelial cell co-culture model," Microbes & Infect. 7(3):448-456.

Brantzaeg et al., 1992, "Compartmentalization of lipopolysaccharide production correlates with clinical presentation in meningococcal disease," J. Infect. Dis. 166(3)650-652.

Bunnell et al., 2000, "A lipid A analog, E5531, blocks the endotoxin response in human volunteers with experimental endotoxemia," Crit. Care Med. 28(8):2713-2720.

Cannon et al., 2008, "Salivary Metabonomics: A New Objective Measure in Oral Care," Poster 14, 8th European Symposium on Saliva, May 14-17, 2008, The Netherlands.

Chapple et al., 2002, "Glutathione in Gingival Crevicular Fluid and Its Relation to Local Antioxidant Capacity in Periodontal Health and Disease," Mol. Pathol. 55(6):367-373.

Ciantar et al., 2002, "Development of an in vitro Microassay for Glucose Quantification in Submicrolitre Volumes of Biological Fluid," J. Periodontal Res. 37(2):79-85.

El Moudni et al., 1995, "Purification and characterisation of a metallopeptidase of Candida albicans," J. Med. Microbiol. 43(4):282-288.

Embery et al., 1994, "Gingival Crevicular Fluid: Biomarkers of Periodontal Tissue Activity," Adv. Dent. Res. 8(2):329-336.

Fokkema et al., 2003, "Monocyte-derived RANTES is intrinsically elevated in periodontal disease while MCP-1 levels are related to inflammation and are inversely correlated with IL-12 levels," Clin. & Exp. Immunol. 131(3):477-483.

Fothergill et al., 1977, "Catabolism of L-Lysine by *Pseudomonas aureuginosa* ," J. Gen. Micriobiol. 99(1):139-155.

Gallegos Olea Olea et al., 2002, "Organic Carbonate from *Caloptropis procera* Leaves," Fitoterapia 73(3):263-265.

Gaspersic et al., 2010, "Anti-NGF treatment reduces bone resorption in periodontitis," J. Dental Res. 89(5):515-520.

Golub et al., 1998, "Modulation of the Host Response in the Treatment of Periodontitis." Dent. Today 17(10):102-6, 108-9

Golub et al., 1997, "A matrix metalloproteinase inhibitor reduces bone-type collagen degradation fragments and specific collagenases in gingival crevicular fluid during adult periodontitis," Inflamm. Res. 46:310-319.

Harrison, 2004, "Physiological Roles of Xanthine Oxidoreductase," Drug Metab. Rev. 36(2):363-375.

Heasman et al., 1993, "Changes in Crevicular Fluid Levels of Interleukin-1 Beta, Leukotriene B4, Prostaglandin E2, Thromboxane B2 and Tumour Necrosis Factor Alpha in Experimental Gingivitis in Humans," J. Periodontal Res. 28(4):241-247.

Ilgenli et al., 2006, "Gingival Crevicular Fluid Matrix Metalloproteinase-13 Levels and Molecular Forms in Various Types of Periodontal Diseases," Oral Dis. 12(6):573-579.

Imbert et al., 2002, "Effect of matrix metalloprotease inhibitors on the 95 kDa metallopeptidase of Candida albicans," J. Antibicrob. Chemother. 49(6):1007-1010.

Ingman et al., 1996, "Matrix metalloproteinases and their inhibitors in gingival crevicular fluid and saliva of periodontitis patients," J. Clin. Periodontol, 23(12):1127-1132.

Ingman et al., 1994, "Multiple Forms of Gelatinases/Type IV Collagenases in Saliva and Gingival Crevicular Fluid of Periodontitis Patients," J. Clin. Periodontol. 21(1):26-31.

International Search Report and Written Opinion in International Application No. PCT/US10/029674 mailed Nov. 12, 2010.

International Search Report and Written Opinion in International Application No. PCT/US10/029670 mailed Aug. 12, 2010.

International Search Report and Written Opinion in International Application No. PCT/US09/039184 mailed Jun. 25, 2010.

International Search Report and Written Opinion in International Application No. PCT/US09/039140 mailed Nov. 27, 2009.

Ishikura et al., 2003, "Cloning of the Tannerella Forsythensis (Bacteriodes Forsythus) siaHI Gene and Purification of the Sialidase Enzyme," J. Med. Micriobiol. 52(Pt. 12):1101-1107.

Jackson et al., 2007, "The Production of Reactive Oxygen and Nitrogen Species by Skeletal Muscle," J. Appl. Physiol. 102(4):1664-1670.

Jahngen et al., 1984, "High-Performance Liquid Chromatography Analysis of Purine Nucleosides in Human Gingival Crevicular Fluid," Arch. Oral Biol. 29(8):607-610.

Karthikeyan et al., 2007, "Gingival Crevicular Fluid and Serum Leptin: Their Relationship to Periodontal Health and Disease," J. Clin. Periodontol. 34(6):467-472.

Kiili et al., 2002, "Collagenase-2 (MMP-8) and collagenase-3 (MMP-13) in adult periodontitis: molecular forms and levels in gingival crevicular fluid and immunolocalisation in gingival tissue," J. Clin. Periodontol. 29(3):224-232; Erratum in: J. Clin. Periodontol. 2004, 31(2):149.

Lamster et al., 2007, "Analysis of Gingival Crevicular Fluid As Applied to the Diagnosis of Oral and Systemic Diseases," Ann. NY Acad. Sci. 1098:216-229.

Lamster, 1997, "Evaluation of Components of Gingival Crevicular Fluid As Diagnostic Tests," Ann. Periodontol. 2(1):123-137.

Lamster et al., 1987, "The Polyamines Putrescine, Spermidine and Spermine in Human Gingival Crevicular Fluid," Arch. Oral Biol. 32(5):329-333.

Lawton et al., 2008, "Analysis of the Adult Human Plasma Metabolome," Pharmacogenomics 9(4):383-397.

Loos et al., 2005, "Host-Derived Diagnostic Markers for Periodontitis: Do They Exist in Gingival Crevice Fluid?" Periodontol. 39:53-72.

(56) References Cited

OTHER PUBLICATIONS

Lorencini et al., 2009, "Changes in MMPs and inflammatory cells in experimental gingivitis," Histol. Histopathol. 24(2):157-166.
Mantyla et al., 2003, "Gingival crevicular fluid collagenase-2 (MMP-8) test stick for chair-side monitoring of periodontitis," J. Periodontol. Res. 38(4):436-439.
McAllister et al., 2008, "Spit Tests: Searching for Biomarkers in the Salivary Proteome," Poster 37, 8th European Symposium on Saliva, May 14-17, 2008, The Netherlands.
Modeer et al., 1996, "Triclosan reduces prostaglandin biosynthesis in human gingival fibroblasts challenged with interleukin-1 in vitro," J. Clin. Periodontol. 23(10):927-933.
Morisseau et al., 1999, "Potent Urea and Carbamate Inhibitors of Solble Epoxide Hydrolases," PNAS 96(16):8849-8854.
Ozmeric, 2004, "Advances in Periodontal Disease Markers," Clin. Chim. Acta 343(1-2):1-16.
Pacher et al., 2006, "Therapeutic Effects of Xanthine Oxidases Inhibitors: Renaissance Half a Century after the Discovery of Allopurinol," Pharmacol. Rev. 58(1):87-114.
Pihlstrom et al., 2005, "Periodontal Diseases," Lancet 366(9499):1809-1820.
Pozo et al., 2005, "Longitudinal analysis of metalloproteinases, tissue inhibitors of metalloproteinases and clinical parameters in gingival crevicular fluid from periodontitis-affected patients," J. Periodontol. Res. 40(3):199-207.
Pradeep et al., 2007, "Gingival Crevicular Fluid Levels of Neopterin in Healthy Subjects and in Patients with Different Periodontal Diseases," J. Periodontol, 78(10):1962-1967.
Prapulla et al., 2007, "Gingival Crevicular Fluid VEGF Levels in Periodontal Health and Disease," J. Periodontol. 78(9):1783-1787.
Preshaw et al., 2004, "Subantimicrobial dose doxycycline as adjunctive treatment for periodontitis. A review," J. Clin. Periodontol. 31(9):697-707.
Qin et al., 2006, "Effect of Minocycline Hydrochloride Ointment on IL-8 in Gingival Crevicular Fluid," Wuhan Daxue Xuebao [Medical Journal of Wuhan University] 27(1):75-78.
Rodier et al., 1999, "A *Candida albicans* metallopeptidase degrades constitutive proteins of extracellular matrix," FEMS Microbiol. Lett. 177(2):205-210.
Ruwanpura et al., 2004, "Prostaglandin E2 regulates interleukin-1beta-induced matrix metalloproteinase-3 production in human gingival fibroblasts," J. Dental Res. 83(3):260-265.
Segal et al., 2000, "Xanthine Oxidase Contributes to Host Defense against *Burkholderia cepacia* in the p47(phox-/-) Mouse Model of Chronic Granulomatous Disease," Infect. Immun. 68(4):2374-2378.
Seymour et al., 2007, "Relationship between Periodontal Infections and Systemic Disease," Clin. Microbiol. Infect. 13(Suppl. 4):3-10.
Sorsa et al., 1990, "The role of gingival crevicular fluid and salivary interstitial collagenases in human periodontal diseases," Arch. Oral Biol. 35 Suppl:193S-196S.
Sugawara, 2003, "Host Defense Mechanisms in Oral Mucosa," Tohoku University Dental Journal 22:11-18.
Szasz et al., 2007, "A Comparison of Arteries and Veins in Oxidative Stress: Producers, Destroyers, Function, and Disease," Exp. Biol. Med. (Maywood) 232(1):27-37.
Taba et al., 2005, "Diagnostic Biomarkers for Oral and Periodontal Diseases," Dent. Clin. North Am. 49(3):551-571.
Teng et al., 1992, "Gingival crevicular fluid gelatinase and its relationship to periodontal disease in human subjects," J. Periodontal Res. 27(5):544-552.
Tervahartiala et al., 2000, "The in vivo Expression of the Collagenolytic Matrix Metalloproteinases (MMP-2, -8, -13, and -14) and Matrilysin (MMP-7) in Adult and Localized Juvenile Periodontitis," J. Dental Res. 79(12):1969-1977.
Toker et al., 2006, "Effect of meloxicam on gingival crevicular fluid IL-1beta and IL1 receptor antagonist levels in subjects with chronic periodontitis, and its effects on clinical parameters," Clin. Oral Investig. 10(4):305-310.
Tsai et al., 2005, "Lipid Peroxidation: A Possible Role in the Induction and Progression of Chronic Periodontitis," J. Periodontal Res. 40(5)378-384.
Tu et al., 2009, "Cyclosporine A enhances apoptosis in gingival keratinocytes of rats and in OECMI cells via the mitochondrial pathway," J. Periodontal Res. 44(6): 767-775.
Valko et al., 2007, "Free Radicals and Antioxidants in Normal Physiological Functions and Human Disease," Int. J. Biochem. Cell Biol. 39(1):44-84.
Van Dyke et al., 2003, "Resolution of inflammtion: A New Paradigm for the Pathogenesis of Periodontal Diseases," J. Dent. Res. 82(2):82-90.
Xu et al., 2004, "Effectiveness of a Triclosan/Copolymer Dentifrice on Microbiological and Inflammatory Parameters," Compend. Contin. Educ. Dent., Medline Database Accession No. NLM15645886.
Yang et al., 2006, "Eukaryotic Pathways for the Induction of Peptidase by Pathogenic Oral Bacteria," D-144, http://ieg.ou.edu/ASM2006/data/papers/D_144.htm.
Yoshimura, 2004, "Recognition of Periodontopathic Bacteria by Innate Immune System," J. Japanese Soc. of Periodontol. 46:94-100.
Yoshioka et al., 2003, "Effect of hydroxamic acid-based matrix metalloproteinase inhibitors on human gingival cells and Porphyromonas gingivalis." J. Periodontol. 74(8):1219-1224.
Abreu et al., 2005, "TLR Signaling in the Gut in Health and Disease," J. Immunol. 174:4453-4460.
Andrian et al., 2005, "Porphyromonas gingivalis Lipopolysaccharide Induces Shedding of Syndecan-1 Expressed by Gingival Epithelial Cells," J. Cellular Physiology 204:178-183.
Brentano et al., 2005, "The Role of Toll-like Receptor Signalling in the Pathogenesis of Arthritis," Cellular Immunology 233:90-96.
Chung et al., 2004, "Innate Immune Response of Oral and Foreskin Keratinocytes: Utilization of Different Signaling Pathways by Various Bacterial Species," Infection and Immunity 72(1):352-358.
Darveau et al., 1998, "Local Chemokine Paralysis, a Novel Pathogenic Mechanism for Porphyromonas gingivalis," Infection and Immunity 66(4):1660-1665.
Eferl et al., 2003, "AP-1: A Double-Edged Sword in Tumorigenesis," Nature Reviews Cancer 3(11):859-868, Abstract.
Foster, N. et al, 2005, "VIP Inhibits Porphyromonas gingivalis LPS—induced immune responses in human monocytes," Journal of Dental Research 84(11):999-1004.
Fu et al., 2008, "Peripheral arterial occlusive disease: Global gene expression analyses suggest a major role for immune and inflammatory responses," BMC Genomics 9:369.
Guha et al., 2001, "LPS Induction of Gene Expression in Human Monocytes," Cellular Signalling 13:85-94.
Huang et al., 2004, "Differential regulation of cytokine genes in gingival epithelial cells challenged by Fusobacterium nucleatum and Porphyromonas gingivalis," Microbial Pathogenesis 37(6):303-312.
Imatani et al, 2000, "Histatin 5 inhibits inflammatory cytokine induction from human gingival fibroblasts by Porphyromonas gingivalis," Oral Microbiology and Immunology 15:378-382.
Koj, 1996, "Initiation of Acute Phase Response and Synthesis of Cytokines," Biochimica et Biophysica Acta 1317:84-94.
Krisanaprakornkit et al., 2000, "Inducible Expression of Human β-Defensin 2 by Fusobacterium nucleatum in Oral Epithelial Cells: Multiple Signaling Pathways and Role of Commensal Bacteria in Innate Immunity and the Epithelial Barrier," Infection and Immunity 68(5):2907-2915.
Lee et al., 2005, "Anti-inflammatory effects of magnolol and honokiol are mediated through inhibition of the downstream pathway of MEKK-1 in NF—κb activation signaling," Planta Medica 71(4):338-343.
McInturff et al., 2005, "Granulysin-derived peptides demonstrate antimicrobial and anti-inflammatory effects against Propionibacterium acnes," J. Investigative Dermatology 125:256-263.
O'Neill, 2004, "TLRs: Professor Mechnikov, Sit on Your Hat," Trends in Immunology 25(12)687-693.
Oteiza et al., 2005, "Zinc, Oxidant-Triggered Cell Signaling, and Human Health," Molecular Aspects of Medicine 26:245-255.

(56) References Cited

OTHER PUBLICATIONS

Rahman, 2003, "Oxidative Stress, Chromatin Remodeling and Gene Transcription in Inflammation and Chronic Lung Diseases," J. Biochemistry Molecular Biology 36(1):95-109.

Roberts et al., 2002, "Beneficial Bacteria of the Periodontum," Periodontology 30:40-50.

Sfakianakis et al., 2001, "Actinobacillus actinomycetemcomitans-induced Expression of IL-1α abd IL-1β in Human Gingival Epithelial Cells: Role in IL-8 Expression," European J. Oral Science 109:393-401.

Singh et al., 2005, "Development of an in vitro screening assay to test the antiinflammatory properties of dietary supplements and pharmacologic agents," Clinical Chemistry 51(12):2252-2256.

Smith et al., 2006, "Cellular and Molecular Aspects of Gastric Cancer," World J. Gastroenterology 12(19):2979-2990.

Takeda et al., 2004, "TLR Signaling Pathways," Seminars in Immunology 16:3-9.

Takeda et al., 2005, "Toll-Like Receptors in Innate Immunity," International Immunology 17(1):1-14.

Tanos et al., 2005, "Phosphorylation of c-Fos by Members of the p38 MAPK Family: Role in the AP-1 Response to UV Light," J. Biological Chemistry 280(19):18842-18852.

Vankeerberghen et al., 2005, "Differential induction of human beta-defensin expression by periodontal commensals and pathogens in periodontal pocket epithelial cells," Journal of Periodontology, 76(8):1293-1303.

\* cited by examiner

METHODS OF MODULATING CELL SURFACE RECEPTORS TO PREVENT OR REDUCE INFLAMMATION

CROSS REFERENCE TO RELATED APPLICATION

This application claims the benefit of U.S. Provisional Patent Application Ser. No. 60/757,751 filed Jan. 10, 2006, the contents of which are incorporated herein by reference.

BACKGROUND OF THE INVENTION

The soft tissues of the mammalian oral cavity are known to exhibit the earliest indications of inflammation. This generalized low level of inflammation may lead to gingivitis and/or periodontitis. Such inflammation is generally believed to be the result, at least in part, by the bacteria present in the oral cavity. Further, oral tissue inflammation can be caused by surgery, localized injury, trauma, necrosis, improper oral hygiene or various systemic origins.

It is generally believed that the cellular components implicated by these diseases and conditions include epithelial tissue, gingival fibroblasts, and circulating leukocytes, all of which contribute to the host response to pathogenic factors generated by the bacteria. Some bacterial pathogens implicated in these oral infections are known although many may remain unknown or uncharacterized. Although the infection by certain types of bacteria is often the etiological event in many of these oral diseases, the pathogenesis of the disease state or condition is mediated by the host response. Use of antibacterial agents reduces the bacterial population of a given oral cavity and may result in a reduction of inflammation. However, this approach is disadvantageous as such killing is accomplished indiscriminately (both beneficial oral bacteria and deleterious oral bacteria may perish) and it is dose and time sensitive.

Bacterial infection of the oral tissue stimulates the host's immune response and diminishes the healing process by up-regulating inflammatory mediators that cause significant tissue damage. These metabolites have been implicated as the prime mediators in gingivitis, periodontitis, osteomyelitis and other inflammatory diseases.

It has been reported that one mechanism of inflammation is mediated through certain transmembrane receptors of mammalian cells. For example, toll-like receptors ("TLRs"), are glycosylated transmembrane proteins and once activated by ligand-induced oligomerization initiate an immune response within the cell, ultimately resulting in the expression of cytokines, interleukins, and other molecules that mediate the state of inflammation.

There is a need in the art for agents and techniques useful in the diagnosis, treatment, and prevention of such inflammatory effects.

BRIEF SUMMARY OF THE INVENTION

Figure 1:
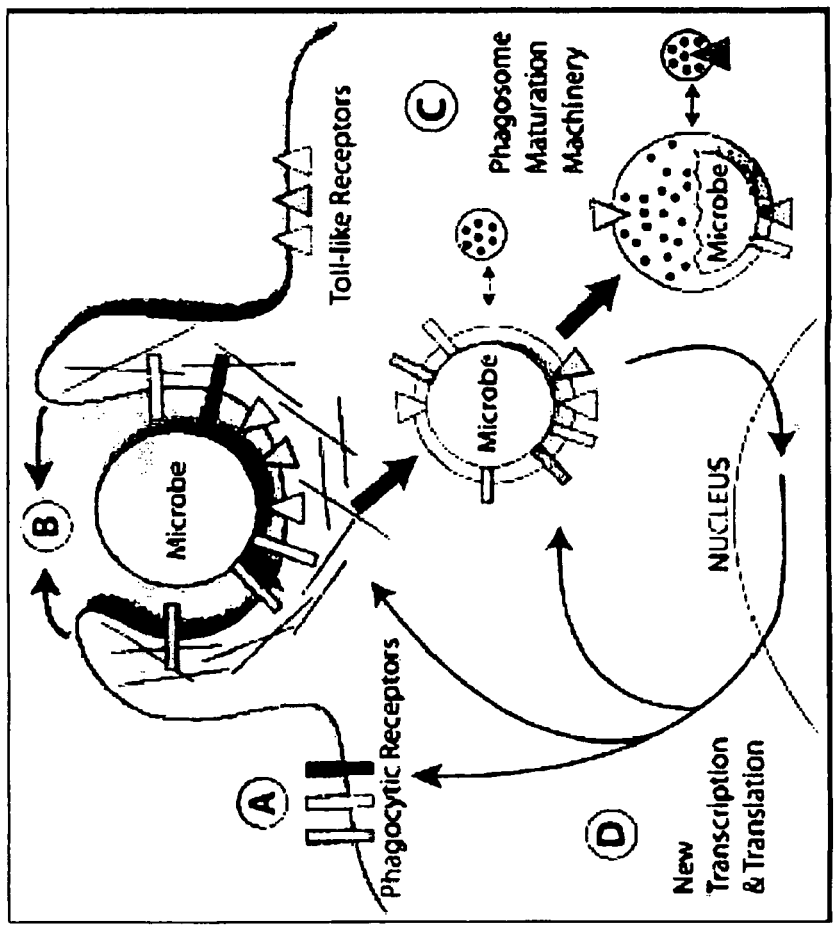
FIG. 1 is a schematic diagram showing a cell's surface in contact with a microbe.

The invention includes a method of distinguishing among oral bacteria species to determine whether a species is orally deleterious. Such method includes contacting at least one bacterium or portion of a bacterium of a species of oral bacteria a gingival cell; and detecting the presence of an indicator compound. The substantial absence of an indicator material signifies that the species of bacteria is not a deleterious species.

Also included within the scope of the invention are methods for determining the anti-inflammatory effect of an agent. Such methods include contacting the cell with the agent in the presence of a deleterious bacterium or portion of such bacterium and detecting the presence of an indicator compound. The substantial absence of an indicator material signifies that agent is an anti-inflammatory agent.

DETAILED DESCRIPTION OF THE INVENTION

The invention provides methods for (1) distinguishing among deleterious bacterial species and beneficial oral bacteria and (2) methods for determining the anti-inflammatory effect of a specific agent. Also provided are methods of preventing the modulation of a toll-like receptor in a cell using triclosan.

"Inflammation" as used herein refers to the localized protective response elicited by injury or destruction of tissues that serves to destroy, dilute, or sequester both the injurious agent and the injured tissue. In the acute form, it may be characterized by pain, heat, redness, and swelling. Histologically, inflammation involves a complex series of events, including dilation of arterioles, capillaries, and venules, with increased permeability and blood flow; exudation of fluids, including plasma proteins, and leukocytic migration into the inflammatory locus. Inflammation corresponds to enhanced levels of pro-inflammatory cellular mediators, or substances that are released for example, as the result of the interaction of an antigen with an antibody or by the action of antigen with a sensitized lymphocyte. By extension, an anti-inflammatory agent is any that reduces the quality and/or quantity of these histological effects in a cell, relative to a like cell not treated with the agent.

The invention provides, in part, a method of evaluating a specific species or strain of bacteria in order to determine whether such species or strain is deleterious in the oral cavity. By "deleterious" it is meant pathogenic bacteria the presence of which results in generation of inflammatory mediators by the affected cells. Some strains/species of bacterial have been reported to be deleterious, including those of Table I, below:

TABLE 1

| Oral Bacteria Reported to Be Deleterious |
|---|
| A. gerencseriae |
| A. naeslundii 1 |
| A. naeslundii 2 |
| V. parvula |
| S. mitis |
| S. oralis |
| C. gingivalis |
| C. sputigena |
| F. nucleatum ss nucleatum |
| F. nucleatum ss polymorphum |
| F. periodonticum |
| P. intermedia |
| T. forsythia |
| L. buccalis |
| N. mucosa |
| P. acnes |
| P. melaninogenica |
| S. noxia |

The method includes contacting at least one bacterium of the species or strain of oral bacteria to be evaluated with at least one gingival cell. Alternatively, the gingival cell can be contacted with a portion of the bacterium, the cell membrane, the cytoplasmic contents, the bacterium's metabolic, end or by-products and/or virulence factors.

This step may occur in vitro, for example, by maintaining culture of bacteria or bacterial parts and of gingival cells and combining such cultures. Alternatively, the contact may occur in vivo, by application of the bacterial culture in an appropriate delivery vehicle to the oral cavity.

Figure 2:
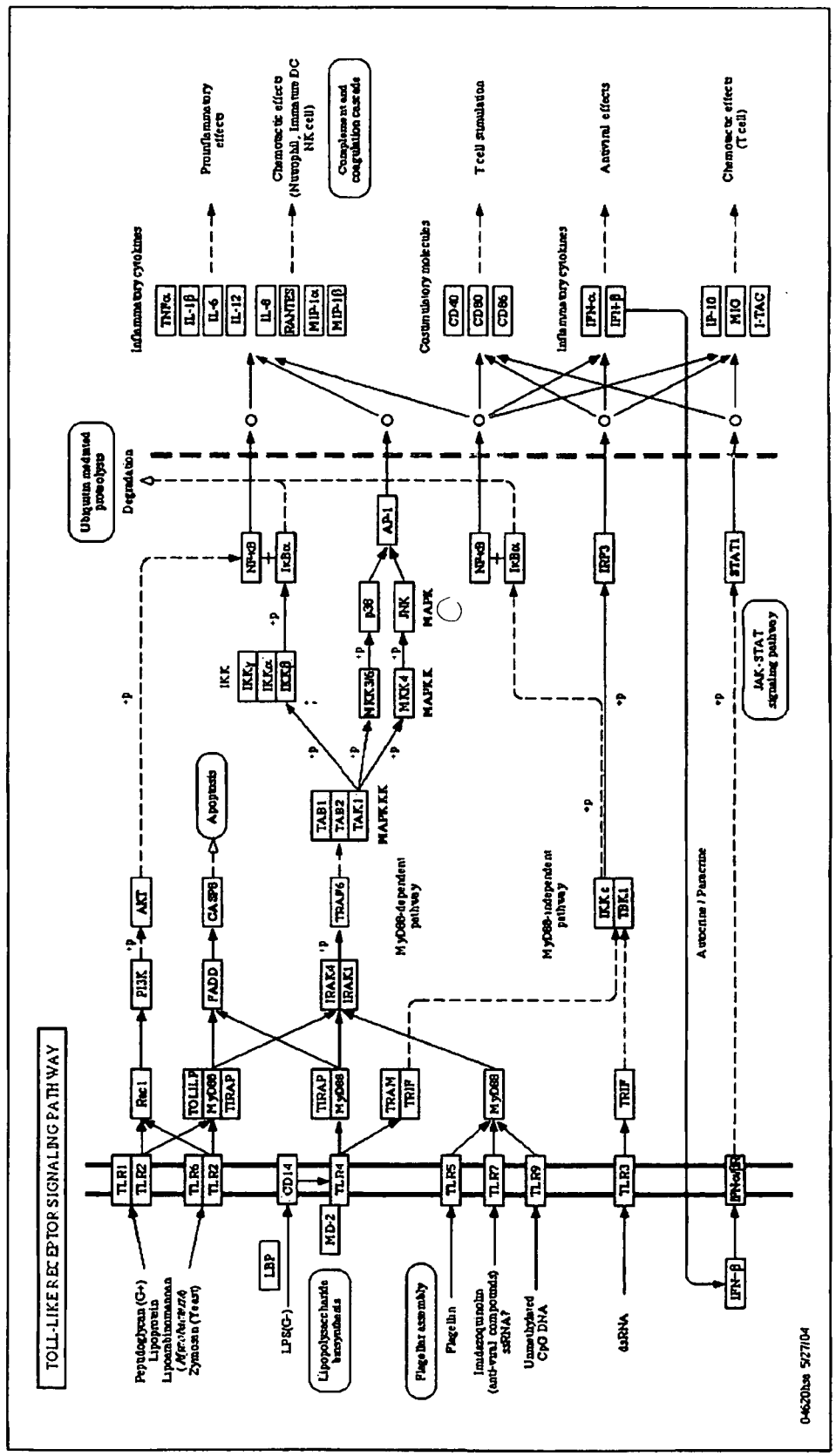
FIG. 2 shows the signaling pathways of toll-like receptors (TLR) 1, 2, 3, 4, 5, 6, 7 and 9, as well as the various molecules generated by the modulation of each TLR.

After such contact, one or more indicator material may be detected. Such indicator materials include any that are know or to be discovered that are generated by in the ordinary course of a host's immune response including intermediate compounds, enzymes, proteins, RNAs, DNAs, and other molecules that are involved in the cellular production of cytokines and other pro-inflammatory mediators. Preferred are indicator materials that are generated by the modulation of any of the toll-like receptors (e.g., as shown in FIG. 2), including, for example, TLRs 2, 3, 4, 5, 7, and 9; molecules of the NFk-B pathway, cytokines, interleukins (e.g., 1, 6, 8, 12), tumor necrotic factor (TNF), peptidases, and mRNAs coding for the interleukin or TNF subunits and/or interleukins, chemokines (e.g., CCL5, CCL4, CCL3, and CC10), and matrix metaloproteinases.

The detection of the selected indicator material may be carried out by in any manner known or to be developed in the art and may be a relative or an absolute measurement. Detection may be accomplished by direct measurement of the quantity of selected indicator material(s). Alternatively, it may be accomplished by indirect measurement using additional detection systems, such as radioactive and/or fluorescent markers, antibodies, alterations in the level of gene expression of specific genes, mRNA analysis, microarray analysis, and/or changes in antioxidant status. For example, if the indicator material is an enzyme, one may subject the sample to an appropriate substrate and measure the end product of an enzyme-catalyzed reaction to determine the presence or absence of the enzyme indicator material. In the practice of this aspect of the invention, the substantial absence of the selected indicator material demonstrates that the species/strain of bacteria is not deleterious—i.e., does not affect the cell in such as manner as to initiate the production of any pro-inflammatory mediators.

The invention also includes a method for evaluating the anti-inflammatory capacity or effect of a specific agent, i.e., the capability of the agent to reduce or eliminate inflammation in a tissue exposed to a pathogenic bacterium. The method includes selection of an agent to be evaluated. Such agent may be a protein, peptide, organic molecule, inorganic molecule or conjugate of any of the same.

Under some circumstances, it may be desirable that the selected agent to be evaluated does not exhibit significant bactericidal effects in the oral context. For example, the agent may be selected from those that exhibit a Minimal Inhibitory Concentration (MIC) of 0, less than about 5%, less than about 10%, less than about 20% and less than about 30%.

MIC studies general include preparation of a solution of the active agent in an appropriate solvent and subsequent serial dilution of the solubilized active. A standard suspension of the selected bacteria (these could be a range of bacteria each of which requires its own specialized protocol for growth and handling) is added to each concentration of the diluted active. The bacteria+active are incubated under appropriate conditions at 37° C. and bacterial growth monitored typically after 48 hours of incubation.

Controls for the MIC studies include a growth control that monitors bacterial growth in the absence of any added solvents or excipients. Additional controls monitor the sterility of the media used for tests. The effects of the solvent(s) used to solubilize the active agents on bacteria are the final series of controls included for these studies.

Following incubation, the plates are read in a microplate spectrophotometer at 610 nm. Results are interpreted as the lowest concentration of the active agent that inhibits the bacterial growth. At high active concentrations, bacteria would not grow (shows as a low optical density reading) and at low active concentrations bacteria would proliferate (shows as a high optical density reading). The lowest active concentration to stop bacterial growth is defined as the MIC. The controls should come out as follows:

Sterility of media—no bacterial growth

Monitoring bacterial growth—the cultures show demonstrate luxurious growth

The solvents used to solubilize active agents should not inhibit bacteria (as they must be essentially innocuous).

The method of evaluating the anti-inflammatory capacity or effect of a specific agent includes the step of contacting a cell with a pathogenic or deleterious bacterium. The cell to be contacted may be in vitro or in vivo, prokaryotic or eukaryotic, and may be obtained from a cell culture line or a clinical sample.

Suitable pathogenic or deleterious bacteria for use in the method include any know or to be discovered in the art that affect the selected cell in such a way as to elicit an immune response. Such bacteria may include, for example, those listed in Table I, above.

The method of evaluating the anti-inflammatory capacity or effect of a specific agent includes the step of detecting the presence or absence of one or more indicator compound(s). Indicator compounds and detection methods and systems may be any of those described above.

Also included in the invention are oral formulations containing the agents found to exhibit an anti-inflammatory effect by the assay described above, as well as methods of preventing the modulation of toll-like receptors on oral tissue cells by contacting such cell with triclosan.

The invention also provides methods of reducing or preventing inflammation of an oral tissue by application of a compound, such as triclosan, to the tissue at sub-MIC levels. By sub-MIC levels.

The invention claimed is:

1. A method of distinguishing among oral bacteria species to determine whether a species is orally deleterious, the method comprising:
   a) contacting at least one bacterium or portion of a bacterium of a species of oral bacteria with a gingival cell in situ in a mammalian cavity; and
   b) detecting the presence of an indicator material wherein the indicator material is generated by a modulation of any of the toll-like receptors or includes molecules of the NFK-β pathway and the indicator material is selected from the group consisting of molecules generated by the modulation of the toll-like receptors and molecules of the NFK-β pathway, and the absence of the indicator material signifies that the species of bacteria is not a deleterious species.

2. The method of claim 1, wherein the indicator material is selected from the group consisting of molecules generated by the modulation of the toll-like receptors and the toll-like receptors being modulated include TLR 2, TLR 3, and TLR4.

3. The method of claim 1, wherein the indicator material is selected from the group consisting of molecules generated by the modulation of the toll-like receptors and the toll-like receptors being modulated include TLR 5, TLR 7, and TLR 9.

4. The method of claim 1, wherein the indicator material is selected from the group consisting of molecules of the NFK-β pathway.

5. The method of claim 1, wherein the indicator material is detected directly.

6. The method of claim 1, wherein the indicator material is detected indirectly.

7. The method of claim 1, wherein the at least one bacterium is obtained from a clinical sample.

* * * * *